(12) United States Patent
Tachibana

(10) Patent No.: US 7,736,856 B2
(45) Date of Patent: Jun. 15, 2010

(54) METHOD OF SCREENING DRUG WITH THE USE OF 67 KDA LAMININ RECEPTOR AND DRUG OBTAINED THEREBY

(75) Inventor: Hirofumi Tachibana, Fukuoka (JP)

(73) Assignee: Kyushu TLO Company, Limited, Fukuoka (JP)

(*) Notice: Subject to any disclaimer, the term of this patent is extended or adjusted under 35 U.S.C. 154(b) by 838 days.

(21) Appl. No.: 10/551,469

(22) PCT Filed: Apr. 1, 2004

(86) PCT No.: PCT/JP2004/004772

§ 371 (c)(1),
(2), (4) Date: Jun. 6, 2006

(87) PCT Pub. No.: WO2004/090541

PCT Pub. Date: Oct. 21, 2004

(65) Prior Publication Data

US 2007/0021321 A1      Jan. 25, 2007

(30) Foreign Application Priority Data

Apr. 1, 2003    (JP) ............................. 2003-097652

(51) Int. Cl.
*G01N 33/53* (2006.01)
(52) U.S. Cl. ...................... 435/7.1; 435/7.23; 530/387.1
(58) Field of Classification Search ............... 435/7.1, 435/7.23; 530/387.1
See application file for complete search history.

(56) References Cited

U.S. PATENT DOCUMENTS 6,410,052 B1    6/2002  Morre et al. ................. 424/468

FOREIGN PATENT DOCUMENTS

WO    WO 99/54356    10/1999

OTHER PUBLICATIONS

Zips et al, 2005, In vivo, 19: 1-8.*
Lee et al, 1999, J Immunol, 163: 6292-6300.*
Kirkin et al, 1998, APMIS, 106 : 665-679.*
Kimmel et al, 1987 (J. Neurosurg, 66:161-171, of record).*
Dermer, 1994 (Bio/Technology, 12:320).*
Kaiser (Science, 2006, 313, 1370).*
Gura, 1997, (Science, 278:1041-1042).*
International Search Report completed May 18, 2004.
Tachibana; "A receptor for green tea polyphenol EGCG."; Natural Structural & Molecular Biology; vol. 11, No. 4, (2004); pp. 380-381.
The Supplementary Europian Search Report dated Mar. 13, 2007, pp. 1-5.
Hou et al.: "Effects of tea polyphonols on signal transduction pathways related to cancer chemoprevention", Mutation Research, Amsterdam, NL, vol. 555, No. 1-2, Nov. 2, 2004; pp. 3-19.
Narumi et al.: "Inhibition of experimental metastasis of human fibrosarcoma cells by anti-recombinant 37-kDa Taminin binding protein antibody", Japanese Journal of Cancer Research, Japanese Cancer Association, Tokyo, JP, vol. 90, No. 4, Apr. 1999, pp. 425-431.
Gevarowska Dorota et al.: "Synthetic peptides interacting with the 67-kd laminin receptor can reduce retinal ischemia and inhibit hypoxia-induced retinal neovascularization", American Journal of Pathology, vol. 160, No. 1, Jan. 2002, pp. 307-313.
Tanaka Masashi et al.: "Expression of the 37-kDa laminin binding protein in murine lung tumor cell correlates with tumor angiogenesis", Cancer Letters, vol. 153, No. 1-2, May 29, 2000, pp. 161-168.
Koo et al.: "Pharmacological effects of green tea on the gastrointestinal system", European Journal of Pharmacology, Amsterdam, NL., vol. 500, No. 1-3, Oct. 1, 2004, pp. 177-185.
Koo et al.: "Pharmacological effects of green tean on the gastrointestinal system", European Journal of Pharmacology, Amsterdam, NL, vol. 500, No. 1-3, October 1, 2004, pp. 177-185.
European Office Action dated Aug. 9, 2009.

* cited by examiner

*Primary Examiner*—Larry R. Helms
*Assistant Examiner*—Minh Tam Davis
(74) *Attorney, Agent, or Firm*—Whitham Curtis Christofferson & Cook, PC

(57) ABSTRACT

It is intended to provide a novel method of screening a drug with the use of a 67 kDa laminin receptor and a drug obtained thereby. A method of screening a drug having an effect on inhibiting cell proliferation, an angiogenesis inhibitory effect, an effect of inhibiting cancer cell metastasis, a neuroprotective effect, and anti-allergic effect, and anti-arteriosclerotic effect and/or an effect of inhibiting infection with Creutzfeldt-Jakob disease which involves the step of qualitatively or quantitatively measuring the degree of the binding of a test compound to a 67 kDa laminin receptor, and judging that the test compound is a drug having an effect of inhibiting cell proliferation, and angiogenesis inhibitory effect, an effect of inhibiting cancer cell metastasis, a neuroprotective effect, and anti-allergic effect, and anti-arteriosclerotic effect and/or an effect of inhibiting infection with Creutzfeldt-Jakob disease in the case where it is found out by the results of the measurement that the test compound binds to the 67 kDa laminin receptor, and a drug obtained thereby.

6 Claims, 6 Drawing Sheets

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: Synthetic oligonucleotide primer

<400> SEQUENCE: 1
atgtccggag cccttgatgt cc                                              22

<210> SEQ ID NO 2
<211> LENGTH: 23
<212> TYPE: DNA
<213> ORGANISM: Artificial
<220> FEATURE:
<223> OTHER INFORMATION: Synthetic oligonucleotide primer

<400> SEQUENCE: 2
ttaagaccag tcagtggttg ctc                                             23

METHOD OF SCREENING DRUG WITH THE USE OF 67 KDA LAMININ RECEPTOR AND DRUG OBTAINED THEREBY

TECHNICAL FIELD

The present invention relates to a screening method for drugs using a 67 kDa laminin receptor, and to a drug obtained by it.

BACKGROUND ART 67 kDa laminin receptor (hereinafter it may be referred to as "67LR") is a protein of 67 kDa, which is derived from a 37 kDa precursor protein translated from mRNA that codes for 295 amino acids, through intracellular acylation polymerization of the precursor protein by a fatty acid for homo-dimerization or hetero-dimerization thereof; and only when it moves onto the surface of a cell membrane together with integlins, it functions as a laminin receptor (*Biochemistry*, 1995, 34: 11276-11287, T. H. Landowski et al.; *J. Cell. Biochem.*, 1998, 69: 244-251, S. Buto et al.). It has been clarified that the 37 kDa precursor protein participates in protein synthesis as a ribosome-related protein p40 and it is the same as that reported as a multidrug resistance-related protein (MGr1-Ag) (*Cell. Mol. Life Sci.*, 2002, 59: 1577-1583, Y. Shi et al.). From the data of its high expression in many types of cancer cells, the laminin receptor is considered to be an oncofetal antigen as an immunogen for T cells, or that is, as a general tumor-specific transplantation antigen (*Anticancer Research*, 1999, 19: 5535-5542, J. H. Coggin, Jr., et al.). In addition to 67LR, a dozen or so types of laminin receptors have been already reported, and of those, the relationship between 67LR and cancer is strongly suggested.

Based on detection or non-detection thereof in cancer cells, 67LR is known as an important prognostic factor in many types of cancers that indicates the degree of malignancy of human cancer patients (*Breast Cancer Research and Treatment*, 1998, 52: 137-145, S. Menard, et al.; *Clinical Cancer Research*, 1997, 3: 227-231, G. Fontanini, et al.; *Clinical Cancer Research*, 1996, 2: 1777-1780, F. Basolo, et al.; *J. Natl. Cancer Inst.*, 1991, 83: 29-36, V. Coice, et al.). In animal models, it is suggested that 67LR participates in proliferation, movement, invasion and metastasis of cancer cells. For example, it is reported that the survival rate of 67LR-positive breast cancer patients is significantly lower than that of 67LR-negative ones. It is shown that the expression of laminin, the ligand of 67LR, has no influence on prognosis but the expression of the receptor 67LR brings about a negative result in prognosis (*Breast Cancer Research and Treatment*, 1998, 52: 137-145, S. Menard, et al.).

Some experiments have been reported, on the basis of this information and with expectation of an antitumor effect by inhibiting 67LR expression. It is reported that a 67LR low-expression cell line constructed by introduction of an anti-sense RNA of 67LR into a cancer cell line shows in-vivo significant depression of tumor proliferation capability and depression of metastasis capability in mice, as compared with the original parent cell strain, and, as a result, it increases the survival rate of individual mice (British Journal of Cancer, 1999, 80: 1115-1122, K. Satoh, et al.). Further, it is reported that the 67LR low-expression cell line retards tumor neovascularization and decrease, the production of a neovascularization promotion factor, VEGF itself, as compared with the parent strain (Cancer Letters, 2000, 153: 161-168, M. Tanaka, et al.). Similarly, also in tumor metastasis experiments using an antibody for 67LR, the same effect as in the antisense experiments has been recognized (Jpn. J. Cancer Res., 1999, 90: 425-431, K. Narumi, et al.).

In the fields not relating to tumor, some reports have been made regarding the function of 67LR. It is reported that the growth of neovascularized blood vessels that are induced in ischemic animal models is inhibited by a 67LR-binding laminin-derived peptide (cysteine-aspartic acid-proline-glycine-tyrosine-isoleucine-glycine-serine-arginine) or EGF-derived peptide (cysteine-valine-isoleucine-glycine-tyrosine-serine-glycine-aspartic acid-arginine-cysteine) (*Am. J. Pathol.*, 2002, 160: 307-313, D. Gebarowska, et al.). It is reported that eNOS expression and NO production, which are said to participate in arteriosclerosis induced by the shear force to angioendothelial cells, are inhibited by a 67LR-binding laminin-derived pentapeptide (tyrosine-isoleucine-glycine-serine-arginine) (*J. Biol. Chem.*, 1999, 274: 15996-16002, T. Gloe, et al.).

A recent report says that 67LR acts as a receptor for a prion protein, which is considered as a cause for Creutzfelds-Jakob disease, and prion binding for internalization and further the binding and the internalization are inhibited by secretion of a membrane domain-deficient mutant 67LR (EMBO J., 2001, 20: 5863-5875, S. Gauczynski, et al.).

It is also reported that 67LR is expressed in a subset group of CD4+CD8− or CD4−CD8+ of CD45RO+/CD45RA− memory cells that are a subset of T cells, and an effect of 67LR to the immune system is suggested (J. Immunol., 1999, 163: 3430-3440, S. M. Canfield, et al.).

There are some reports relating to the expression of mRNA of 67LR. It is reported that the expression is inhibited by a cancer-inhibiting factor p53 or anticancer factors TNF-alpha and IFN-gamma (*Biochem. Biophys. Res. Commun.*, 1998, 251: 564-569, N. Clausse, et al.). However, there is no report relating to low-molecular compounds for 67LR which is presumed to participate in such diverse functions.

On the other hand, among catechins, epigallocatechin gallate (hereinafter this may be referred to as "EGCG") is an main ingredient of tea catechins, accounting for about 50% thereof. In addition, tea catechins include epigallocatechin, epicatechin gallate and epicatechin (hereinafter these may be referred to as "EGC", "ECG" and "EC", respectively).

There is a long history that tea has been used as a drug from the past, and recently, tea has been analyzed for the relation between its efficacy and its components. Of the components, EGCG is a component discovered by A. Bradfield, et al. in 1947 (J. Chem. Soc., 1947, 32: 2249, A. E. Bradfield, et al.).

Various physiological effects of tea catechins including EGCG have been reported, for example, antioxidation, anti-cancer, suppression of plasma cholesterol increase, suppression of blood pressure increase, platelet aggregation inhibition, suppression of blood sugar increase, dementia prevention, antiulcer, antiinflammation, antiallergy, antibacterial, anticaries, antiviral, detoxication, enteroflora improvement, deodorization (*Functions of Tea*, edited by Keiichiro Muramatsu, Society Publishing Center, 2002).

Of those, there are many reports relating to anticancer effect that includes anti-mutation effect, anti-carcinogenic promotion effect, antitumor proliferation-inhibiting effect, anti-invasion/metastasis inhibiting effect, anti-neovascularization inhibiting effect. Recent reports say that EGCG inhibits DNA synthesis in leukemia cells, thereby inducing apoptosis (*Int. J. Mol. Med.*, 2001, 7: 645-652, D. M. Smith, et al.), and that GCG inhibits the growth of breast cancer cells (*J. Cell. Biochem.*, 2001, 82: 387-398, K. T. Kavanagh, et al.). Further, there is a report saying that EGCG inhibits the proliferation of cancer cells more strongly than that of normal cells (Arch. Biochem. Biophys., 2000, 376: 338-346, N. Ahmad, et al.).

Regarding invasion and metastasis, it is reported that catechin inhibits the invasion of high-metastatic cells in an invasion test using a matrigel, and that EGCG inhibits adhesion of cancer cells to fibronectin and laminin (Cancer Lett., 1995, 98: 27-31, M. Susuka, et al.; Cell Biol. Int., 1993, 17: 559-564, M. Isemura, et al.; Cancer Lett., 2001, 173: 15-20, Y. Suzuki, et al.).

Further, molecular-level analysis of these catechin effects has been reported recently. For example, EGCG concentration-dependently inhibits the proliferation of Her-2 antigen high-expression cells which, as suggested, may have relation to cancer. As reported, its functional mechanism would be inhibition of the downstream signal transmission through Her-2 phosphorylation inhibition (Cancer Res., 2002, 62: 652-655, S. Pianetti, et al.).

It has been reported that catechins including EGCG inhibit neovascularization which has close relationship with tumor growth. As indicated, the mechanism is that catechins inhibit the phosphorylation of VEGFR-1, a receptor for VEGF, which is a growth factor for angioendothelial cells. It is reported that this does not depend on the antioxidation and anti-radical activity of catechins (Cancer Res., 2002, 62: 381-385, S. Lamy, et al.).

Similarly, it is reported that catechins inhibit the phosphorylation of PDGF-R-beta by another growth factor, PDGF-BB in vascular smooth muscle cells, thereby inhibiting the hypertrophy of blood vessels (FASEB J., 2002, 16: 893-895, A. Sachinidis, et al.).

Further, it is reported that EGCG inhibits in-vivo neovascularization and growth of endothelial cells by EGF-2 (Nature, 1999, 389: 381, Y. Cao, et al.). There is a report saying that EGCG binds to an apoptosis-inducing Fas protein (Biochem. Biophys. Res. Commun., 2001, 285: 1102-1106, S. Hayakawa, et al.). However, it is not clarified as to whether the above-mentioned EGCG's effect could have relation to Fas, but suggesting the presence of any other factor that may interact with EGCG.

It has become clear on the molecular level that catechins have various physiological effects in addition to the antitumor effect thereof. It is reported that EGCG inhibits glucose production in hepatic cells and promotes tyrosine phosphorylation of the insulin receptor and IRS-1, and is therefore effective against diabetes (J. Biol. Chem., 2002, 277: 34933-34940, M. E. Waltner-Law, et al.).

From a report indicating that, in Parkinson model mice, EGCG shows a strong neuroprotective effect (J. Biol. Chem., 2002, 277: 30574-30580, Y. Levites, et al.), EGCG is expected to inhibit many types of neuropathy. There are a report saying that the expression of Fc-epsilon RI in basophils, which is a cause for allergy, is inhibited by EGCG and its methylated derivative (J. Agric. Food Chem., 2002, 50: 5729-5734, Y. Fujimura, et al.); and a report saying that the expression of COX-2 and NO synthase-2, as induced by IL-1-beta in cartilage, is inhibited by EGCG (Free Radical Biology & Medicine, 2002, 33: 1097-2002, S. Ahmed, et al.).

However, so long as the present inventors know, there is no report at all up to the present, relating to the fact that EGCG functions as a cell growth-inhibiting factor via 67LR and to the fact that 67LR may be used as a target in drug screening for low-molecular compounds having a cell growth-inhibiting effect.

(Non-Patent Reference 1)
 Biochemistry, 1995, 34: 11276-11287

(Non-Patent Reference 2)
 J. Cell. Biochem., 1998, 69: 244-251

(Non-Patent Reference 3)
 Cell. Mol. Life Sci., 2002, 59: 1577-1583

(Non-Patent Reference 4)
 Anticancer Research, 1999, 19: 5535-5542

(Non-Patent Reference 5)
 Breast Cancer Research and Treatment, 1998, 52: 137-145

(Non-Patent Reference 6)
 Clinical Cancer Research, 1997, 3: 227-231

(Non-Patent Reference 7)
 Clinical Cancer Research, 1996, 2: 1777-1780

(Non-Patent Reference 8)
 J. Natl. Cancer Inst., 1991, 83: 29-36

(Non-Patent Reference 9)
 Breast Cancer Research and Treatment, 1998, 52: 137-145

(Non-Patent Reference 9)
 British Journal of Cancer, 1999, 80: 1115-1122

(Non-Patent Reference 10)
 Cancer Letters, 2000, 153: 161-168

(Non-Patent Reference 11)
 Jpn. J. Cancer Res., 1999, 90: 425-431

(Non-Patent Reference 12)
 Am. J. Pathol., 2002, 160: 307-313

(Non-Patent Reference 13)
 J. Biol. Chem., 1999, 274: 15996-16002

(Non-Patent Reference 14)
 EMBO J., 2001, 20: 5863-5875

(Non-Patent Reference 15)
 J. Immunol., 1999, 163: 3430-3440

(Non-Patent Reference 16)
 Biochem. Biophys. Res. Commun., 1998, 251: 564-569

(Non-Patent Reference 17)
 J. Chem. Soc., 1947, 32: 2249

(Non-Patent Reference 18)
 Functions of Tea, edited by Keiichiro Muramatsu, Society Publishing Center, 2002

(Non-Patent Reference 19)
 Int. J. Mol. Med., 2001, 7: 645-652

(Non-Patent Reference 20)
 J. Cell. Biochem., 2001, 82: 387-398

(Non-Patent Reference 21)
 Arch. Biochem. Biophys., 2000, 376: 338-346

(Non-Patent Reference 22)
 Cancer Lett., 1995, 98: 27-31

(Non-Patent Reference 23)
 Cell. Biol. Int., 1993, 17: 559-564

(Non-Patent Reference 24)
 Cancer Lett., 2001, 173: 15-20

(Non-Patent Reference 25)
 Cancer Res., 2002, 62: 652-655

(Non-Patent Reference 26)
 Cancer Res., 2002, 62: 381-385

(Non-Patent Reference 27)
 FASEB J., 2002, 16: 893-895

(Non-Patent Reference 28)
Nature, 1999, 389: 381

(Non-Patent Reference 29)
Biochem. Biophys. Res. Commun., 2001, 285: 1102-1106

(Non-Patent Reference 30)
J. Biol. Chem., 2002, 277: 34933-34940

(Non-Patent Reference 31)
J. Biol. Chem., 2002, 277: 30574-30580

(Non-Patent Reference 32)
J. Agric. Food Chem., 2002, 50: 5729-5734

(Non-Patent Reference 33)
Free Radical Biology & Medicine, 2002, 33: 1097-2002

DISCLOSURE OF THE INVENTION

The present inventors conducted extensive studies in consideration of the above-mentioned problems, and, as a result, have found that 67LR can be used as a target for drugs having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect, and have completed the present invention.

Specifically, the invention is as follows:

[1] A method of screening a drug having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect, which comprises a step of qualitatively or quantitatively determining the degree of binding of a test compound to a 67 kDa laminin receptor, and, when the test compound binds to the 67 kDa laminin receptor from the test data, then judging that the test compound is a drug having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect.

[2] The screening method of [1], wherein the drug has a cell growth-inhibiting effect, a neovascularization-inhibiting effect and/or a cancer cell metastasis activity-inhibiting effect.

[3] A drug obtainable according to the screening method of [1] or [2].

[4] The drug of any of [1] to [3], wherein the active ingredient is a compound having a galloyl group.

[5] The drug of [4], wherein the compound is a catechin.

[6] The drug of [5], wherein the catechin is epigallocatechin gallate.

[7] The drug of any of [3] to [6], which is used for a disease capable of being prevented and/or treated owing to the cell growth-inhibiting effect, the neovascularization-inhibiting effect, the cancer cell metastasis activity-inhibiting effect, the neuroprotective effect, the anti-allergic effect, the anti-arteriosclerotic effect and/or the Creutzfelds-Jakob disease infection-inhibiting effect thereof.

[8] The drug of any of [3] to [6], which is used for a disease capable of being prevented and/or treated owing to the cell growth-inhibiting effect, the neovascularization-inhibiting effect and/or the cancer cell metastasis activity-inhibiting effect thereof.

[9] The drug of [8], wherein the disease is cancer.

[10] A method for producing a pharmaceutical composition, which comprises a step of producing the drug of any of [3] to [9] by chemical synthesis, and a step of adding a pharmaceutically acceptable carrier thereto.

[11] A pharmaceutical composition obtainable according to the production method of [10].

[12] A screening method for a drug, which comprises a step of qualitatively or quantitatively determining the degree of binding of a compound having a galloyl group and a test compound to a 67 kDa laminin receptor, and, when the degree of binding of the test compound with the 67 kDa laminin receptor is higher than that of binding of the compound having a galloyl group to the 67 kDa laminin receptor from the test data, then judging that the test compound is a drug having the same pharmacological effect as that of catechins.

[13] A screening method for a drug, which comprises a step of making competition between the binding of a compound having a galloyl group to a 67 kDa laminin receptor and the binding of a test compound to the 67 kDa laminin receptor, and as a result of the competition, when the site at which the test compound has bound with the 67 kDa laminin receptor is the same as the site at which the compound having a galloyl group has bound with the 67 kDa laminin receptor, then judging that the test compound is a drug having the same pharmacological effect as that of the compound having a galloyl group.

[14] The screening method of [12] or [13], wherein the pharmacological effect of the compound having a galloyl group is a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect.

[15] The screening method of [12] or [13], wherein the pharmacological effect of the compound having a galloyl group is a cell growth-inhibiting effect, a neovascularization-inhibiting effect and/or a cancer cell metastasis activity-inhibiting effect.

[16] The screening method of any of [12] to [15], wherein the compound is a catechin having a galloyl group.

[17] The screening method of any of [12] to [15], wherein the catechin is epigallocatechin gallate.

[18] A drug obtainable according to the screening method of any of [12] to [17].

[19] The drug of [18], which is used for a disease capable of being prevented and/or treated owing to the cell growth-inhibiting effect, the neovascularization-inhibiting effect, the cancer cell metastasis activity-inhibiting effect, the neuroprotective effect, the antiallergic effect, the antiarteriosclerotic effect and/or the Creutzfelds-Jakob disease infection-inhibiting effect thereof.

[20] The drug of [18] or [19], which is used for a disease capable of being prevented and/or treated owing to the cell growth-inhibiting effect, the neovascularization-inhibiting effect and/or the cancer cell metastasis activity-inhibiting effect thereof.

[21] The drug of [20], wherein the disease is cancer.

[22] A method for producing a pharmaceutical composition, which comprises a step of producing the drug of any of [18] to [21] by chemical synthesis, and a step of adding a pharmaceutically-acceptable carrier thereto.

[23] A pharmaceutical composition obtainable according to the production method of [22].

[24] A compound capable of binding to a 67 kDa laminin receptor at a site thereof that is the same as the site at which a compound having a galloyl group binds to the 67 kDa laminin receptor.

[25] The compound of [24], which is a catechin.

[26] The compound of [26], wherein the catechin is epigallocatechin gallate.

[27] A cell growth inhibitor containing the compound of any of [24] to [26].

[28] A neovascularization inhibitor containing the compound of any of [24] to [26].

[29] A cancer cell metastasis activity inhibitor containing the compound of any of [24] to [26].

[30] An anticancer agent inhibitor containing the compound of any of [24] to [26].

BEST MODE FOR CARRYING OUT THE INVENTION

Figure 1:
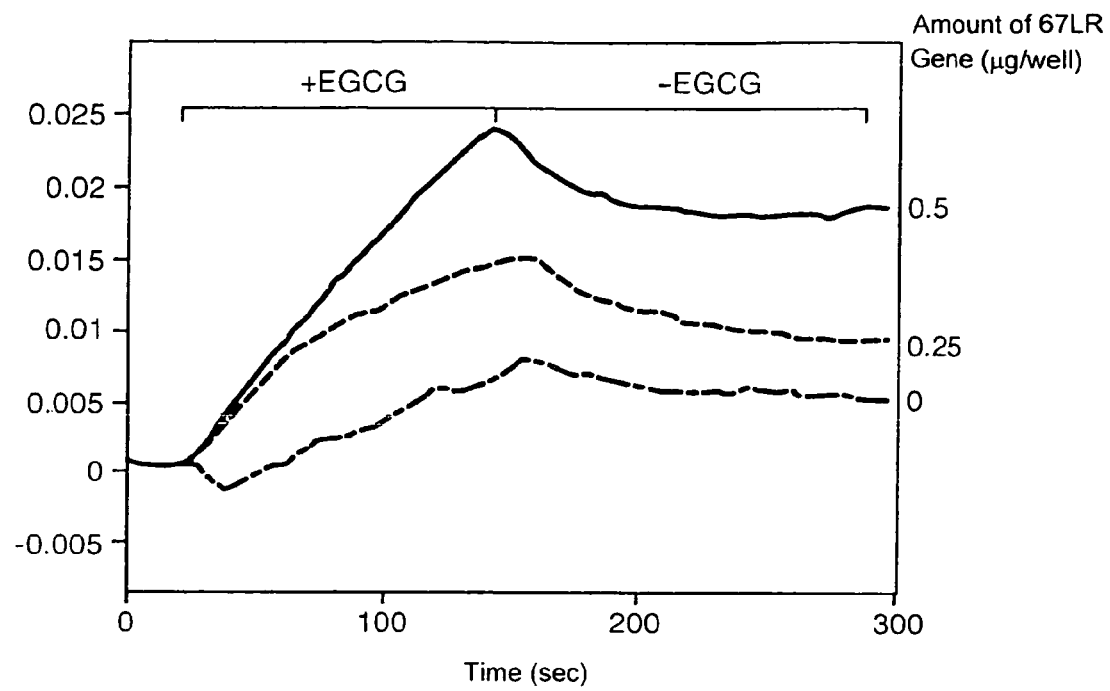
FIG. 1:
It is a drawing showing the test data with a surface plasmon resonance sensor in Example 1.

The invention is described in detail hereinunder.

The invention provides a novel screening methods for drugs, using 67LR as a target.

One embodiment of the invention is a screening method for drugs having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect, which comprises a step of qualitatively or quantitatively determining the degree of binding of a test compound to a 67 kDa laminin receptor, and, when the test compound binds to the 67 kDa laminin receptor from the test data, then judging that the test compound is a drug having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect.

67LR used in the present invention itself is a known protein, and, for example, based on GenBank Accession No. NM-002295 registered cDNA sequence, cDNA of 67LR can be readily obtained according to an ordinary process by using the PCR with a template of various libraries to sandwich the sequence which encoding the present protein therebetween. The cDNA thus obtained may be inserted into various commercially-available vectors in the form that enables protein expression, whereby it is easy to construct a cell line capable of expressing the present protein and to obtain the present protein itself. Apart from it, there are some reports relating to cDNA production and protein expression (*Proc. Natl. Acad. Sci. U.S.A.*, 1988, 85: 6394, H. You, et al.; *British Journal of Cancer*, 1999, 80: 1115-1122, K. Satoh, et al.; *Biochemistry*, 1995, 34: 11276-11287, T. H. Landowski, et al.).

As a gene thereof, 67LR is a 40S ribosome-binding protein of 37 kDa, but it is known that when the protein is expressed in membranes, it has 67 kDa. In the invention, any and every protein that has 67 kDa when expressed in membranes and has the ability of adhesion to bind to laminin is defined as 67LR for use in the present invention. Not only an intact protein, but also its partial peptide can be used herein. Depending on the means for screening employed herein, 67LR may be used in any form of, for example, a purified protein, or a soluble protein, or a protein bonded to a carrier, or a protein fused with any other protein.

In the invention, a test compound is bound with 67LR whereby drugs are screened for those having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect. The test compound in this step is not particularly limited and may have any form of cell extracts, cell culture supernatants, fermented microorganism products, organism extracts, plant extracts, purified or crude proteins, peptides, non-peptidic compounds, synthetic low-molecular compounds, natural compounds, gene libraries and others that are used in ordinary drug screening.

For the binding of a test compound to 67LR, any suitable mode may be selected in accordance with the form of the test compound used. For example, a method of adding a test compound to a culture of 67LR expressing cells may be used.

In the manner as above, the degree of binding of a test compound to 67LR is determined. The method for the determination to be employed herein may be any of a qualitative method or a quantitative method. One example of the method of determining the binding degree comprises using a surface plasmon resonance sensor as demonstrated in Examples given hereinunder.

As a result of the measurement of the binding degree thereof, when the test compound has substantially bound to 67LR, then the test compound is judged to be a drug having a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect. Above all, the screening method of the invention is favorable for drugs having a cell growth-inhibiting effect, a neovascularization-inhibiting effect and/or a cancer cell metastasis activity-inhibiting effect.

As demonstrated in Examples given hereinunder, a compound having a galloyl group which is suggested to have a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect has bound with 67LR and has extremely inhibited the cell growth.

This suggests that a compound having a galloyl group may function as a cell growth factor via 67LR, further indicating that, like the compound having a galloyl group, a substance capable of binding to 67LR may have the same effects as those of the compound having a galloyl group, which are a cell growth-inhibiting effect, a neovascularization-inhibiting effect, a cancer cell metastasis activity-inhibiting effect, a neuroprotective effect, an anti-allergic effect, an anti-arteriosclerotic effect and/or a Creutzfelds-Jakob disease infection-inhibiting effect.

Accordingly, in the screening method of the invention, it may be judged that a test compound capable of binding to 67LR is a drug having a cell growth-inhibiting effect, a neovascularization-inhibiting effect, a cancer cell metastasis activity-inhibiting effect, a neuroprotective effect, an anti-allergic effect, an anti-arteriosclerotic effect and a Creutzfelds-Jakob disease infection-inhibiting effect.

The compound having a galloyl group mentioned above includes galloyl group-having catechins such as epigallocatechin gallate and its 3-methyl-substituted derivative, and epicatechin gallate; galloyl group-having polyphenols; and trigalloylglucose, pentagalloylglucose, strictinin, pyrogallol. Preferred is epigallocatechin gallate.

Other embodiments of the screening method of the invention are described.

In other embodiments thereof, the invention provides a screening method for drugs, using a compound having a galloyl group in addition to 67LR. Specifically, the screening method for drugs comprises a step of qualitatively or quantitatively determining the degree of binding of a compound having a galloyl group and a test compound to 67LR, and, when the degree of binding of the test compound to 67LR is higher than that of binding of the compound having a galloyl group to 67LR from the test data, then judging that the test compound is a drug having the same pharmacological effect as that of the compound having a galloyl group.

The invention also provides a screening method for drugs, which comprises a step of making competition between the binding of a compound having a galloyl group to a 67 kDa laminin receptor and the binding of a test compound to the 67 kDa laminin receptor, and as a result of the competition, when the site at which the test compound has bound to the 67 kDa laminin receptor is the same as the site at which the compound having a galloyl group has bound to the 67 kDa laminin receptor, then judging that the test compound is a drug having the same pharmacological effect as that of the compound having a galloyl group.

As demonstrated in Examples given hereinunder, a monoclonal antibody to 67LR interferes with the binding of a compound having a galloyl group to 67LR, therefore interfering with the cell growth-inhibiting effect of a compound having a galloyl group. Contrary to this, a compound having a galloyl group interferes with the binding of an anti-67LR antibody to 67LR. Specifically, the binding site of a compound having a galloyl group overlaps with the antibody-recognition site thereof. This indicates that, in competitive reaction of a compound having a galloyl group and a test compound with 67LR, when the test compound has bound at the same site as that at which the compound having a galloyl group has bound, then the test compound may be considered to have the same effect as that of the compound having a galloyl group.

The screening method of the other embodiment of the invention not using a compound having a galloyl group has been described in detail hereinabove, and its description shall apply to the embodiments of the invention using a compound having a galloyl group. The compound having a galloyl group as referred to herein for use in the screening method of these embodiments of the invention may be suitably diluted with a buffer such as PBS before its use, as in Examples given hereinunder. In case where a test compound and a compound having a galloyl group are added to a 67LR expression cell culture to induce the intended competitive reaction therein, the order of adding the test compound and the compound having a galloyl group thereto is not specifically limited.

The drugs screened as above are usable as those for diseases capable of being prevented and/or treated owing to the cell growth-inhibiting effect, the neovascularization-inhibiting effect, the cancer cell metastasis activity-inhibiting effect, the neuroprotective effect, the anti-allergic effect, the anti-arteriosclerotic effect and/or the Creutzfelds-Jakob disease infection-inhibiting effect thereof. Of those diseases, the invention is the most suitable for cancer.

In the invention, once a drug is selected through the screening, the drug may then be produced through ordinary chemical synthesis. In addition, a pharmaceutically-acceptable carrier may be added thereto. Accordingly, a method for producing a pharmaceutical composition which comprises a step of producing the drug obtainable in the above-mentioned screening method, through chemical synthesis, and a step of adding a pharmaceutically-acceptable carrier thereto; and the pharmaceutical composition obtainable according to the production method are within the scope of the invention.

When the drug is used as a pharmaceutical composition thereof, then the pharmaceutically-acceptable carrier therein includes, for example, physiological saline, vegetable oil, emulsifier, suspending agent, surfactant, stabilizer. The drug may be suitably combined with any of these and may be formulated into a pharmaceutical composition. It may be administered to patients in any mode of, for example, intraarterial injection, intravenous injection, subcutaneous injection or oral administration. Depending on the drug and on the body weight, the age and the condition of the patient, the administration route may be suitably selected. Similarly, the does may be suitably selected and determined depending on the drug and on the body weight, the age and the condition of the patient. When a test compound may be encoded by a DNA thereof, then the DNA can be inserted into a gene therapy vector for carrying out gene therapy with it.

A compound capable of binding to 67LR at a site thereof that is the same as the site at which a compound having a galloyl group binds to 67LR is also within the scope of the invention. As demonstrated in Examples given hereinunder, this is well supported by the following: A monoclonal antibody to 67LR interferes with the binding of a compound having a galloyl group to 67LR, therefore interfering with the cell growth-inhibiting effect of a compound having a galloyl group. Contrary to this, a compound having a galloyl group interferes with the binding of an anti-67LR antibody to 67LR. Specifically, the binding site of a compound having a galloyl group overlaps with the antibody-recognition site thereof. Since the compound of the type is considered to have the same effect as that of a compound having a galloyl group, it is usable as a cell growth inhibitor, a neovascularization inhibitor and a cancer cell metastasis activity inhibitor, or that is, as an anticancer agent.

EXAMPLES

The invention is described in more detail with reference to the following Examples, to which, however, the invention should not be limited.

Materials and Methods (1) Cells and Cell Culturing:

The human lung cancer cell line A549 (ATCC Number: CCL-185) used in this experiment were subcultivated and kept in an ERDF medium (Kyokutoh Pharmaceutical) supplemented with 10% fetal bovine serum (FBS) (Bio Source International, Camarillo, Calif.), at 37° C. in a water vapor-saturated 5% $CO_2$ condition. 1.125 g of $NaHCO_3$ (Wako Pure Chemicals, Osaka, Japan) was added to one liter of the ERDF medium. The cells were cultivated and kept in their logarithmic growth phase. Human Burkit's lymphoma cell line DND39 were subcultivated and kept in a 5% FBS-added RPMI-1640 medium (Nissui, Japan) at 37° C. in a water vapor-saturated 5% $CO_2$ condition. To the RPMI-1640 medium, were added 100 U/ml penicillin (Meiji Pharmaceutical Company, Tokyo, Japan), 100 mg/ml streptomycin (Meiji Pharmaceutical Company), 12.5 mM $NaHCO_3$ (Wako Pure Chemicals), and 10 mM HEPES (Wako Pure Chemicals).

(2) Green Tea Catechins:

Green tea catechins, epigallocatechin-3-O-gallate (EGCG), epicatechin-3-O-gallate (ECG), epigallocatechin (EGC), epicatechin (EC), catechin (C) and epigallocatechin-3-(3-O-methyl)-gallate (EGCG3"Me) were dissolved in a phosphate buffer (PBS) to have a concentration of 5 mM. Before use, it was suitably thawed. PBS was prepared by dissolving 8.0 g of NaCl (Nacalai Tesque, Inc.), 0.2 g of KCl (Nacalai Tesque, Inc.), 1.15 g of $Na_2HPO_4$ (Nacalai Tesque, Inc.) and 0.2 g of $KH_2PO_4$ (Nacalai Tesque, Inc.) in 1 liter of ultra-pure water.

Caffeine and quercetin were purchased from Nacalai Tesque, Inc., and the former was suspended in PBS while the latter was in dimethylsulfoxide (DMSO) (Nacalai Tesque, Inc.), each having a concentration of 5 mM.

(3) Reagents and Instruments:

Tripanblue (Wako Pure Chemicals) was suspended in PBS to have a concentration of 1%, and sterilized in an autoclave at 121° C. for 20 minutes. All-trans-retionic acid (ATRA) was purchased from Sigma (St. Louis, Mo.), and dissolved in ethanol.

TRIzol used for RNA extraction was purchased from Invitrogen (Carlsbad, Calif.). Aqueous 0.1% diethyl pyrocarbonate (DEPC) was purchased from Sigma (St. Louis, Mo.). A DEPC solution used for RNA dissolution was prepared by adding DEPC to distilled water to have a final concentration of 0.1%, then stirring it for 2 hours and autoclaving it. Oligotex-dT30 and human placenta-derived RNase inhibitor were purchased from Takara (Kyoto, Japan); and Molony murine leukemia virus (MMLV)-reverse transferase was purchased from Amersham Pharmacia Biotech (Buckinghamshire, UK). We asked BIOSYNTHESIS (Japan) to synthesize oligonucleotides such as primers. Taq DNA polymerase was purchased from Fermentas (Vilnius, Lithuania), and Ex Taq was purchased from Takara. For polymerase chain reaction (PCR), used was GeneAmp PCR System 2400 (Parkin-Elmer, Tokyo, Japan). As an agarose, used was ultra-pure agarose (Sawaday Technology, Tokyo, Japan).

As a cloning vector, used was $pT_{ARGE}T^{TM}$ Mammalian Expression Vector System (Promega, Madison, Wis.). For purification, used was QIAGEN Plasmid Midi Kit or EndoFree Plasmid Maxi Kit (both QIAGEN).

An LB medium was prepared by dissolving 10 g of Bacto Tryptone (Becton Dickinson, Sunnyvale, Calif.), 5 g of Bacto Yeast Extract (DIFCO LABORATORIES, Detroit, Mich.) and 5 g of NaCl in 1 liter of ultra-pure water, and autoclaving it. After cooled to 60° C., 1000 ml of ampicillin (150 mg/ml) (prepared by dissolving ampicillin sodium (Wako Pure Chemicals) in ultra-pure water to have a concentration of 150 mg/ml and filtering it for sterilization) was added to it. For an LB plate, 2 g of Bacto Tryptone, 1 g of Bacto Yeast Extract, 2 g of NaCl and 5 g of Bacto Agar (DIFCO) were dissolved in 200 ml of ultra-pure water and autoclaved. After cooled to 60° C., 200 ml of ampicillin (150 mg/ml) was added to it, and this was put into 10-ml dishes (Falcon), as divided into portions of 10 ml each. Isopropyl-b-D(-)-thiogalactopyranoside (IPTG) was purchased from Wako Pure Chemicals, and it was formulated to have a concentration of 0.1 M. 5-Bromo-4-chloro-3-indolyl-b-D-galactopyranoside (X-gal) (Wako Pure Chemicals) was dissolved in N,N-dimethylformamide (Wako Pure Chemicals) to have a concentration of 20 mg/ml. SOC was prepared as follows: $H_2O$ was added to 3 g of Bacto Tryptone, 0.75 g of Bacto Yeast Extract, 0.078 g of NaCl and 0.017 g of KCl so as to make 148.5 ml in total. The solution was autoclaved. 1.5 ml of 2 M $Mg^{2+}$ solution (12.324 g of $MgSO_4.7H_2O$ and 10.165 g of $MgCl_2.6H_2O$ were mixed with ultra-pure water to make 50 ml) that had been autoclaved separately from it was added to it. 1 ml of 2 M glucose was added to 100 ml of this solution.

For a DNA sequencer, used was ABI PRISM 310 Genetic Analyzer (Applied Biosystems, Tokyo, Japan), in which was used ABI PRISM BigDye™ Terminator Cycle Sequencing Ready Reaction Kits Version 2.0 (Applied Biosystems). Template Suppression Reagent (TSR) was purchased from Applied Biosystems.

For gene introduction, FuGENE™ 6 Transfection Reagent (Roche Diagnistics Gmbh, Mannheim, Germany) was used.

The anti-human laminin receptor antibody for flow cytometry analysis was purchased from NEOMARKERS (Fremont, Calif.). As a negative control antibody, mouse IgM antibody, used was one from Zymed Laboratories Inc. (San Francisco, Calif.). A fluorescein isothiocyanate (FITC)-labeled anti-mouse IgM goat antibody was purchased from Southern Biotechnology Associates, Inc. (Birmingham, Ala.). In a flow cytometer, used was FACS Calibur (Becton Dickinson).

(4) RNA Extraction and cDNA Synthesis:

Cells that had been previously treated with 1 mM ATRA at 37° C. for 24 hours were washed with PBS, and Trizol was added thereto in an amount of 1 ml per $1 \times 10^7$ cells, and immediately suspended and completely dissolved. After left statically at room temperature for 5 minutes, 0.2 ml of chloroform was added to it and vigorously stirred by turning it upside down. Then, after statically kept at room temperature for 3 minutes, it was centrifuged at 12000×g and at 4° C. for 15 minutes. 0.5 ml of 2-propanol was added to the centrifuged supernatant, and vigorously stirred by turning it upside down. Then, after statically kept at room temperature for 10 minutes, it was centrifuged at 12000×g and at 4° C. for 10 minutes. The supernatant was removed, and the precipitate was rinsed with 1 ml of 75% ethanol. This was centrifuged at 12000×g and at 4° C. for 5 minutes, and the supernatant ethanol was removed as much as possible. The precipitated total RNA was dissolved in 20 ml of aqueous DEPC. cDNA synthesis was carried out as follows: First, 1 ml of $(dT)_{20}$ primer (0.5 mg/ml) was added to 10 mg of the total RNA, left at 70° C. for 10 minutes, and then immediately cooled with ice for annealing. Next, 2 ml of 10 mM dNTP, 0.1 ml of RNase inhibitor, and 4 ml of 5× buffer attached to MMLV-reverse transferase were added to it, and aqueous DEPC was added to it to make 20 ml in total. The resulting mixture was kept at 37° C. for 1 hour for cDNA synthesis, and it was kept at 97° C. for 5 minutes to inactivate the enzyme.

(5) Construction of 67 kDa Laminin Receptor (67LR Expression vector):

DND39 cells were treated with 1 mM ATRA at 37° C. for 24 hours, then subjected to RNA extraction and to cDNA synthesis. With reference to the full-length cDNA (Yow, et al., Proc. Natl. Acad. Sci. USA., 85: 6394-6398 (1988)), primers were produced (H-LamininR-F; 5'-ATGTCCGGAGCCCT-TGATGTCC-3' (SEQ ID NO: 1), H-LamininR-R; 5'-TTAA-GACCAGTCAGTGGTTGCTC-3') (SEQ ID NO: 2). The primers were prepared at 20 mM. 1 ml of the synthesized cDNA, 0.1 ml of Ex Taq, 2 ml of 10 × Taq buffer, 1.6 ml of 2.5 mM DNTP, primers of 0.5 ml each, and 14.3 ml of $dH_2O$ were suspended and subjected to PCR. The condition was as follows: The initial denaturation was at 95° C. for 5 minutes, the denaturation reaction was at 94° C. for 30 seconds, the annealing was at 58° C. for 30 seconds, and the extension reaction was at 72° C. for 30 seconds. 25 cycles of denaturation, annealing and extension were carried out. This was subjected to electrophoresis with 1.2% agarose gel, and the intended band was purified by the use of Wizard SV Gel and PCR Clean-Up System (Promega). Its sequencing confirmed that this is the intended product. 4.18 ml of $dH_2O$ was added to 1 ml of T4 DNA Ligase 10× buffer, 1 ml of $pT_{ARGE}T^{TM}$. Vector, 1 ml of T4 DNA Ligase and 2.80 ml of the PCR product, and kept at 4° C. overnight for ligation. The following operation is the same as that for subcloning. After reciprocal judgment through colony PCR, the colonies were gathered with a platinum loop and transferred into an LB medium, and cultured by shaking therein overnight at 37° C. and at 150 rpm. The cells were collected and purified by the use of EndoFree Plasmid Maxi Kit. Its sequencing confirmed that this is 67LR.

(6) Construction of Transient Expression System for 67LR:

The 67LR expression vector constructed ($pT_{ARGE}T$-hLamininR) was introduced into A549 cells, using FuGENE™ 6 Transfection Reagent. Its details are described below. The cells were inoculated into a 10% FBS-ERDF medium at $1 \times 10^4$ cells/ml. By keeping at 37° C. for 24 hours, the cells were adhered to the medium. Next, a fresh ERDF medium was put into a tube, and FuGENE™ 6 (three times the amount of the gene) was directly added and gently mixed. Next, $pT_{ARGE}T$-hLamininR was added and gently mixed, and this was kept at room temperature for 30 minutes. This was added to the medium, and kept at 37° C. for 48 hours. The cells were washed with a medium, and then the medium was changed with a fresh one.

(7) Influence of Various Components on 67LR Forced Expression Cells:

Various components of various concentrations were added to the 67LR transient expression cells, and treated in a 5% FBS-containing ERDF medium at 37° C. for 48 hours. After the treatment, the number of the cells was counted, and the survival rate of the cells was determined according to a Tripanblue staining method.

Regarding EGCG pretreatment, an anti-67LR antibody having a final concentration of 10 μg/ml (1% FBS-containing ERDF medium) was treated at 37° C. for 30 minutes, and then EGCG treatment was carried out so as to investigate the influence thereof on the antibody-treatment cells. As a negative control, the same treatment was carried out with mouse IgM.

(8) Analysis of Various Components for Their Binding to 67LR Forced Expression Cells:

The binding of various component (5 μM) to the cells was determined by using a surface plasmon resonance sensor SPR670 (Nippon Laser and Electronic Lab., Nagoya, Japan). For the measurement, the cells were fixed on a gold membrane (Nippon Laser and Electronic Lab.) according to a standard fixation method for protein. Precisely, a gold membrane was dipped in a solution in ethanol of 10 mM of 4,4-dithiodibutyric acid, DDA (Tokyo Kasei Kogyo Co., Ltd., Tokyo, Japan) (this was prepared by dissolving 2.38 mg of DDA in 10 ml of 99% ethanol followed by diluting it with ethanol to 1/100) in such a manner that its gold surface could face upward, and gently stirred at room temperature for 30 minutes. Next, this was washed twice with ethanol with no pressure applied to the gold surface to thereby introduce a self-assembly membrane (SA membrane). 25 mg of a water-soluble carbodiimide, EDC (Wako Pure Chemicals) was dissolved in 1 ml of ultra-pure water; and 15 mg of N-hydroxysuccinimide, NHS (Wako Pure Chemicals) was dissolved in 9 ml of 1,4-dioxane (Nacalai Tesque, Inc.). These solutions were mixed, and the SA membrane-processed gold membrane was dipped into the mixture, and gently stirred at room temperature for 10 minutes. 10 ml of ultra-pure water was added, and further stirred at room temperature for 5 minutes. This was washed twice with ultra-pure water with no water pressure applied to the gold surface thereof, then dried (in air), and mounted on a cartridge. The cells were suspended to a density of $3 \times 10^5$ cells/ml (in a flow buffer, PBS), and 20 μl of the cell suspension was dropwise applied onto the gold membrane and kept at room temperature for 30 minutes so as to fix the cells onto the membrane. Next, a green tea catechin diluted with PBS to have a concentration of 1, 10, 25 or 50 μM was applied thereto, and the change in the surface plasmon resonance angle was determined so as to monitor its binding to the cells.

The binding competition test of EGCG and an anti-67LR antibody was carried out as follows: An anti-67LR antibody having a final concentration of 10 μg/ml (1% FBS-containing ERDF medium) was treated at 37° C. for 30 minutes, and then the cells were fixed on the gold membrane and tested in the same manner as above using a surface plasmon resonance sensor. In this case, the same treatment was also carried out with mouse IgM as a negative control.

(9) Flow Cytometry Analysis:

It is known that 67LR is expressed on cell surfaces. Therefore, 67LR expressed on the surfaces of the cells was detected through flow cytometry analysis using an anti-human laminin receptor (LR) antibody. The cells were collected, and using a 1.5-ml Eppendorf tube, they were added to 100 μl, as a whole, of 1% FBS-PBS at $1 \times 10^6$ cells therein. A primary antibody, anti-human LR antibody was added to it to have a final concentration of 10 μg/ml. This was incubated at 4° C. for 30 minutes, and then washed once with PBS. Next, a secondary antibody, anti-mouse IgM FITC-labeled antibody capable of recognizing an isotype of LR antibody was added to 25 μl, as a whole, of 1% FBS-PBS so as to have a final concentration of 12.5 μg/ml. This was incubated at 4° C. for 30 minutes, then washed twice with PBS, and re-suspended in PBS, and analyzed with a flow cytometer. A negative control IgM antibody of the same concentration (10 μg/ml) was reacted in the same manner as herein. The 67LR expression amount on the cell surfaces was indicated by the center value of the fluorescent intensity of LR.

For the purpose of investigating the influence of EGCG treatment on the cell surface expression of 67LR, the cells were treated with an EGCG-added 1% FBS-PBS having a final EGCG concentration of 50 μM, and then kept at 37° C. for 30 minutes. This was washed once with PBS. Then, this was treated in the same manner as above with the primary antibody and others, and analyzed. As a control, the cells were treated with an EGCG-free 1% FBS-PBS.

(10) Statistical Analysis:

The test data were subjected to statistical analysis according to Student's t-test.

Example 1

Influence of 67LR Gene Introduction on the Cell Binding and the Cell Growth Activity of EGCG Using FuGENE™ 6 Transfection Reagent, a 67LR expression vector ($pT_{ARGE}T$-hLamininR) was introduced into A549 cells according to the method mentioned below. The cells were inoculated at $1\times10^4$ cells/ml (10% FBS-ERDF medium). After 24 hours, a fresh ERDF medium was put into a tube, and FuGENE™ 6 (three times the amount of the gene) was directly added and gently mixed. Next, $pT_{ARGE}T$-hLamininR of varying concentrations were added and gently mixed, and this was kept at room temperature for 30 minutes. This was added to the medium, and was continuously cultured at 37° C. for 48 hours. EGCG of various concentrations were added to the 67LR transient expression cells, and treated with a 5% FBS-containing ERDF medium at 37° C. for 48 hours. After the treatment, the number of the cells was counted and the survival rate thereof was determined according to a Tripanblue staining method.

As a result, EGCG concentration-dependent cell growth inhibition was observed in the cells where 67LR was transiently expressed. In addition, in proportion to the 67LR gene amount introduced into the cells, cell growth inhibition was also observed.

67LR is a membrane protein existing in a cell membrane, and the fact that the EGCG effect was enhanced in the cells with the gene expression vector introduced therein would be due to the increase in the EGCG binding. Accordingly, the EGCG binding to the cells was determined by the sue of a surface plasmon resonance sensor. EGCG was used at 5 µM.

Only a little angle change (indicating binding amount) was found in the A549 cells with an empty vector introduced therein. In the cells with 0.25 µg of the 67LR expression vector introduced therein, a great increase in the angle was found; and in those with 0.5 µg thereof introduced therein, a further greater increase in the angle was found. This indicates that the 67LR expression vector introduction increases the binding of EGCG to cell surfaces.

Figure 2:
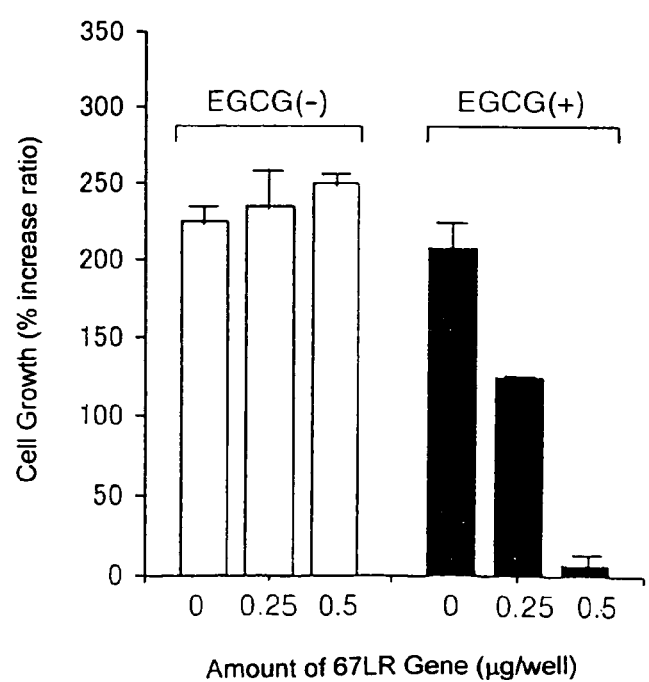
FIG. 2:
It is a drawing showing a result of the cell growth test in Example 1.
Figure 3:
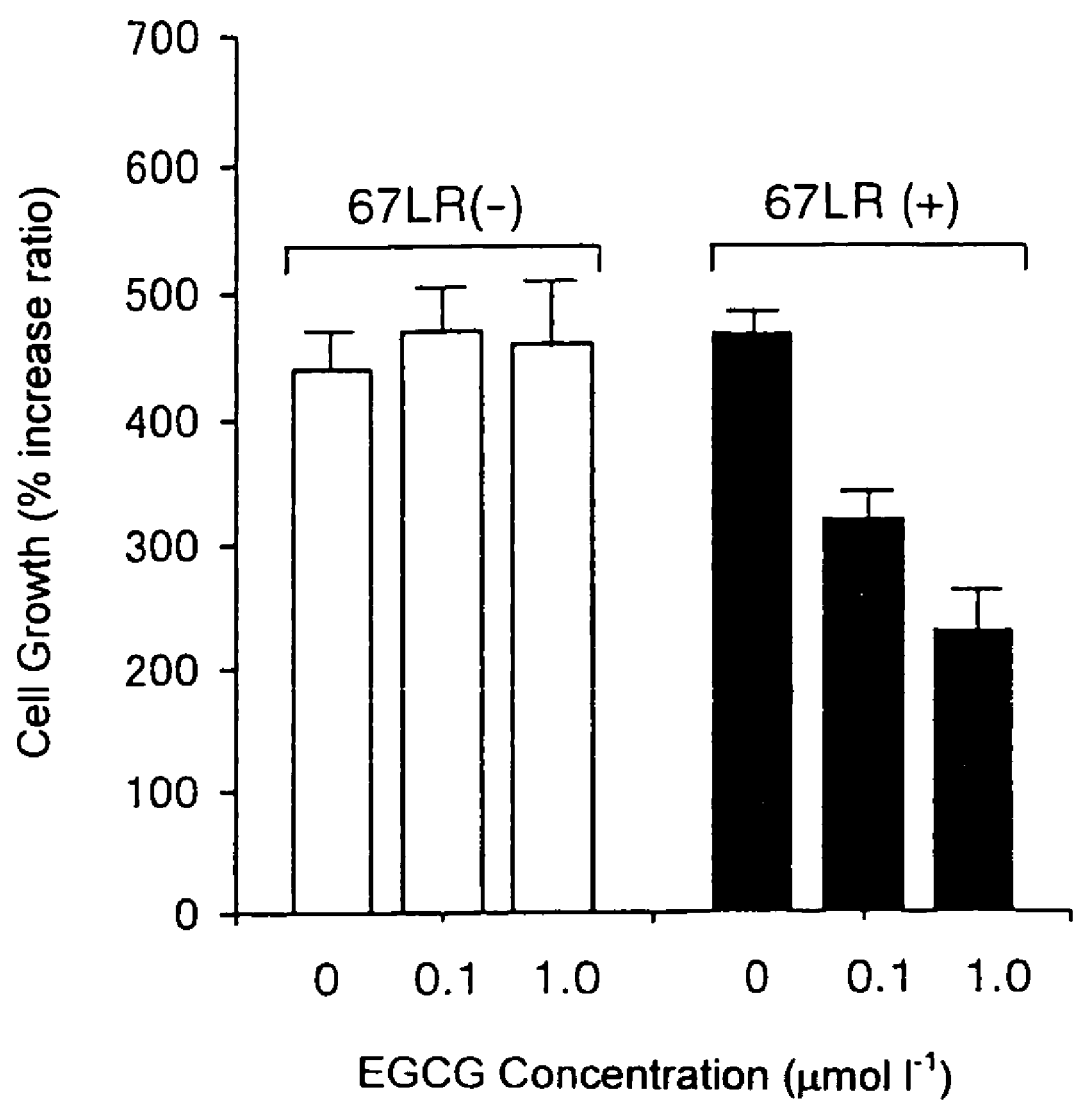
FIG. 3:
It is a drawing showing a result of the cell growth test in Example 1.

The results of Example 1 are shown in FIG. 1, FIG. 2 and FIG. 3.

Example 2

Determination of 67LR Expression Amount on Cell Surfaces

The above indicates that the 67LR expression vector introduction increases the binding of EGCG to cell surfaces. Then, it was investigated as to whether the increase in the binding was caused by the increase in the 67LR expression on the cell membranes, using the flow cytometry.

The 67LR expression amount on the cell surfaces was determined. A little expression was found in the control, A549 cells. An empty vector (0.5 µg) was introduced into the cell showed almost no influence on the expression amount. However, when the 67LR expression vector (0.5 µg) was introduced into the cells, then the expression amount greatly increased. This confirms the expression of 67LR on the cell surfaces.

Further, in order to clarify as to whether EGCG binds to the cells via 67LR, EGCG was allowed to act on the cells before the anti-67LR antibody was allowed to act on them. As a result, the 67LR expression seen in the control cells apparently disappeared. The same phenomenon was found in cells with the empty vector introduced thereinto. In addition, it was the same with the 67LR-introduced cells. From this, it is understood that EGCG previously allowed to act on the cells in advance immediately bound to 67LR on the cell surfaces and therefore the anti-67LR antibody could not bind to 67LR on the cell surfaces and, as a result, the apparent 67LR expression could not be detected.

These results clearly show that the 67LR vector introduction increases the 67LR expression on cell surfaces, also indicating that the increase in the EGCG binding is the increase in the 67LR expression in cell membranes. In addition, it was suggested that EGCG binds to cells via 67LR. Specifically, it was shown that 67LR is a receptor of EGCG.

Figure 4:
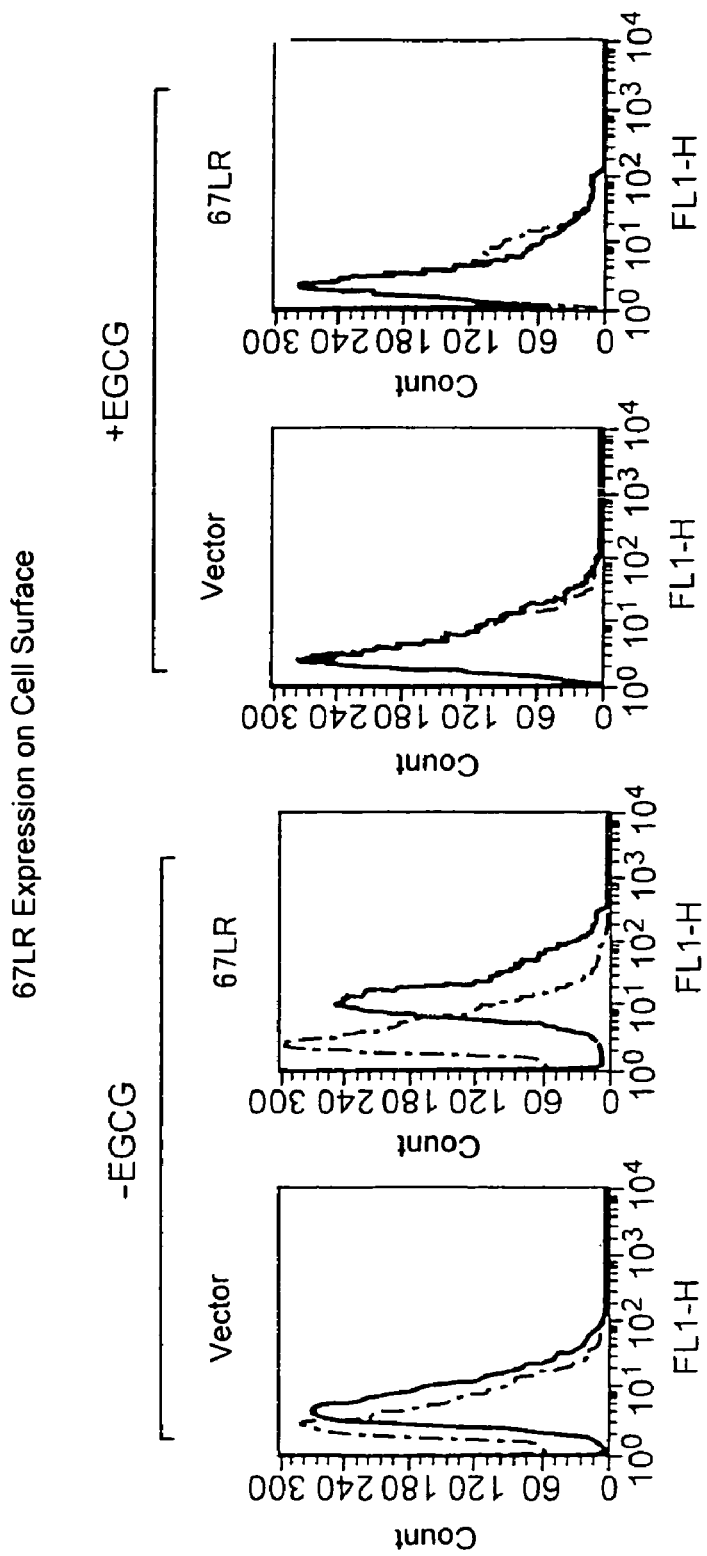
FIG. 4:
It is a drawing showing a result of analysis through flow cytometry in Example 2.

The results in Example 2 are shown in FIG. 4.

Example 3

Influence of Anti-67LR Antibody on the Binding and the Growth Inhibiting Activity of EGCG It was shown that EGCG binds to cells via 67LR and exhibits its growth inhibiting activity. To further clarify this, 67LR forced expression cells were treated in advance with an anti-67LR antibody, and then the influence on the binding and the growth inhibiting activity of EGCG was investigated.

First, the influence of the antibody on the binding was investigated by using a surface plasmon resonance sensor. When an anti-67LR antibody was allowed to act on the cells, then the reduction in the EGCG binding speed and also in the EGCG binding amount itself was formed the angle change. This result was not found in the cells treated with a negative control antibody.

In addition, the influence of the antibody on the cancer cell growth inhibition by EGCG was also investigated. EGCG of a concentration of only 0.1 µM showed its growth inhibiting activity in 67LR forced expression cells. When the cells were subjected to antibody treatment before treating with EGCG, the growth inhibiting activity was lost. In this test, no influence on the survival rate was found. It was shown that not only the EGCG binding to cells but also the growth inhibiting activity of EGCG is exerted via the binding of 67LR to EGCG.

Figure 5:
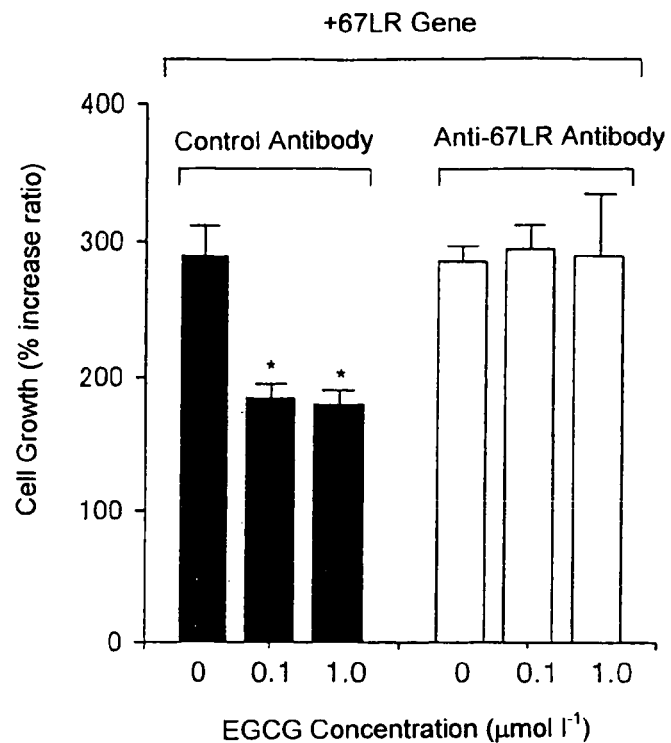
FIG. 5:
It is a drawing showing a result of the cell growth test in Example 3.
Figure 6:
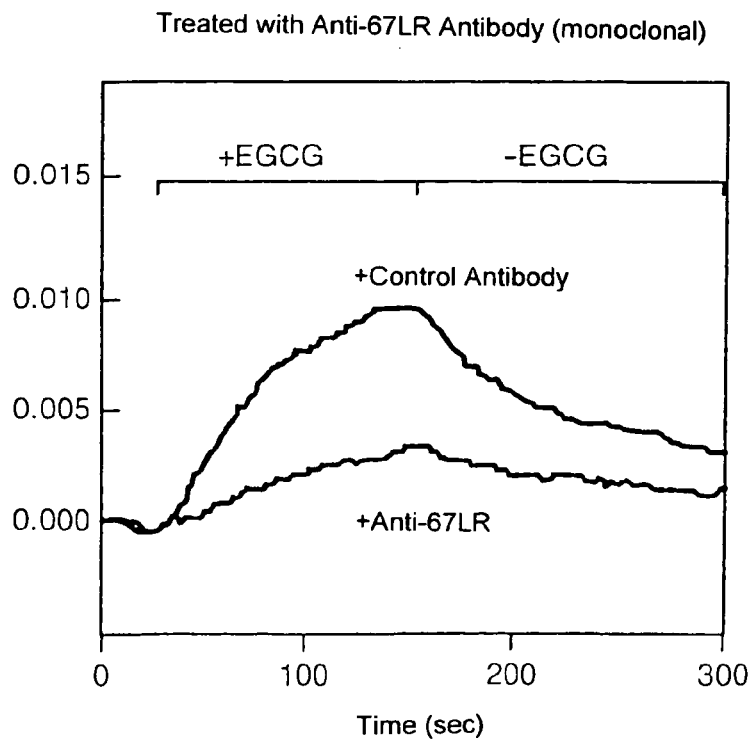
FIG. 6:
It is a drawing showing the test data with a surface plasmon resonance sensor in Example 3.

The results in Example 3 are shown in FIG. 5 and FIG. 6.

Example 4

Influence of 67LR Expression on the Binding and the Growth Inhibiting Activity of Other Tea Components It was shown that EGCG binds to cell membranes via 67LR and it exhibits a cancer cell growth inhibiting activity. It was further investigated whether these effects via 67LR may be intrinsic to EGCG. The other tea components tested herein are principal green tea catechins, ECG, EGC, EC, C, and EGCG3"Me which is reported to have a strong antiallergic effect and to stably exist in vivo. In addition, caffeine that has various physiological functions like catechins, and quercetin, one kind of flavanols that is reported also to have many physiological functions were also tested.

First, the influence of the substances on the growth of 67LR forced expression cells was investigated. Similarly to the above, 0.5 µg of $pT_{ARGE}T$-hLamininR was introduced into A549 cells by the lipofection method, followed by cultivation at 37° C. for 48 hours. Then, the cells were treated with various tea components each having a final concentration of 5 µM. The cells were further cultivated at 37° C. for 48 hours, and then the number of the cells and the survival rate thereof were determined. As a result, the gene introduction has no influence on the survival rate and the number of the cells treated with any of C, EC, EGC, caffeine and quercetin. On the other hand, however, the cells treated with any of ECG and EGCG3"Me both having a galloyl group like EGCG showed the increase in the growth inhibiting effect thereof, like those treated with EGCG. These results suggest that the galloyl group-having components exhibit a growth inhibiting activity in 67LR forced expression cells.

In addition, the binding of various tea components to 67LR forced expression cells was determined by using a surface plasmon resonance biosensor. C, EC and EGC showed no binding to A549 cells, and there was no change also in 67LR forced expression cells. In addition, caffeine and quercetin also did not show cell binding, showing no change also in the forced expression cells. ECG and EGCG"3Me both showed cell binding though not comparable to that of EGCG, and it was clarified that their cell binding increased in 67LR forced expression cells.

Figure 7:
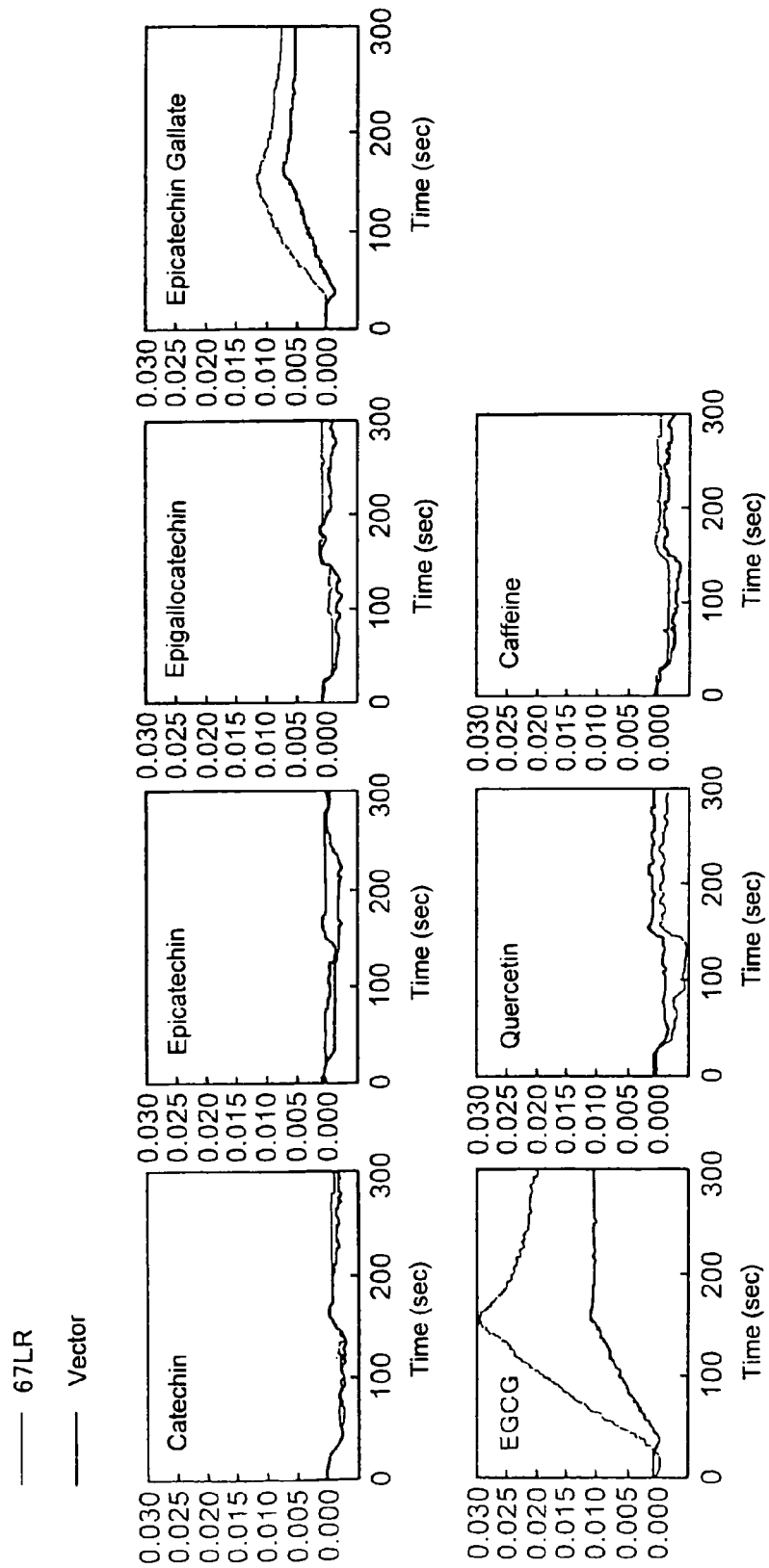
FIG. 7:
It is a drawing showing the test data with a surface plasmon resonance sensor in Example 4.
Figure 8:
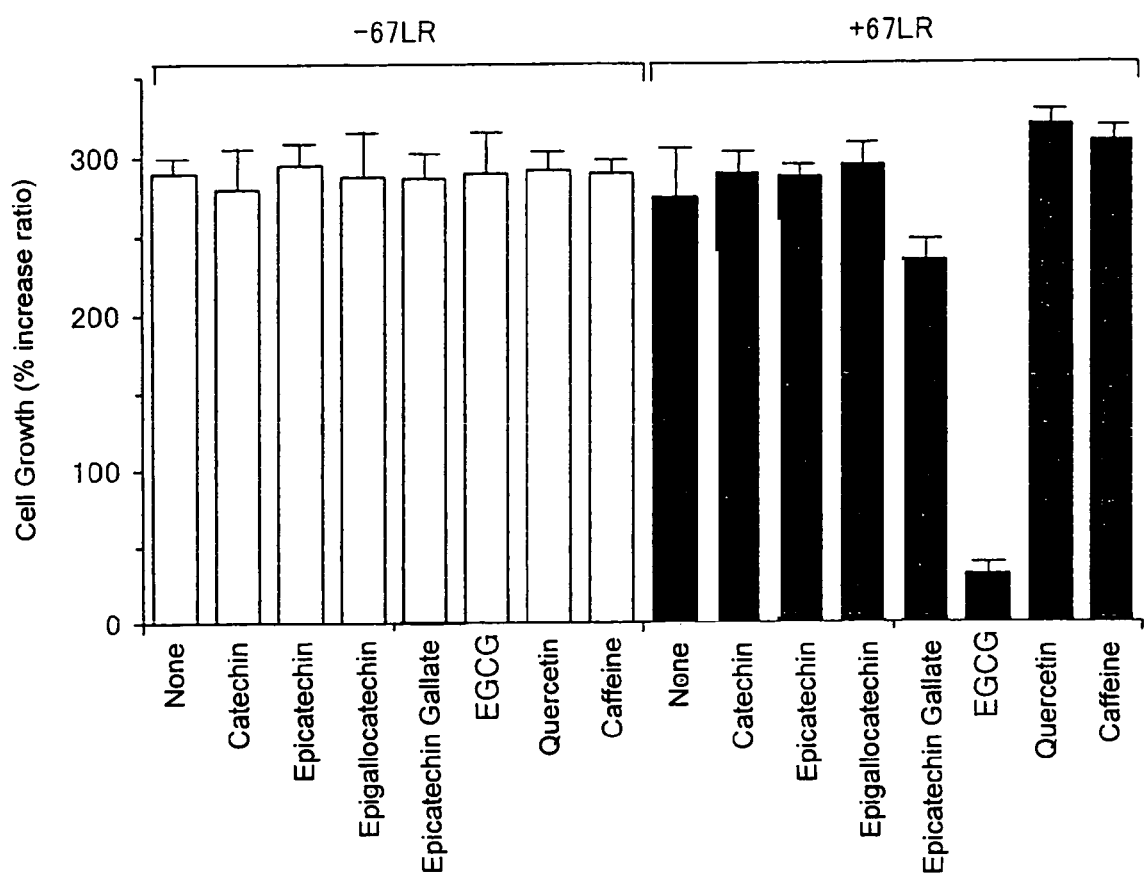
FIG. 8:
It is a drawing showing a result of the cell growth test in Example 4.

The results in Example 4 are shown in FIG. 7 and FIG. 8.

INDUSTRIAL APPLICABILITY

The invention can provide a novel screening method for drugs, using a 67 kDa laminin receptor as a target.

The present application was filed, claiming a priority to Japanese Patent Application No. 2003-097652.

the full length 67 kDa laminin receptor expressed on the cell surface of cancer cells, wherein displacement of the binding of epigallocatechin gallate by the catechin or antibody indicates that the screened catechin or antibody has the same pharmacological effect as that of epigallocatechin gallate, wherein the pharmacological effect of epigallocatechin gallate is a growth-inhibiting effect on cancer cells.

2. A method of screening a catechin or antibody to determine whether the catechin or antibody has the same pharmacological effect as that of epigallocatechin gallate, which comprises the steps of making a competition between the binding of the epigallocatechin gallate to a full length 67 kDa laminin receptor expressed on the cell surface of cancer cells and the binding of the catechin or antibody to the full length 67 kDa laminin receptor expressed on the cell surface of cancer cells, and determining that the catechin or antibody displaces the binding of epigallocatechin gallate to the full length 67 kDa laminin receptor expressed on the cell surface of cancer cells, wherein

---

---

The invention claimed is:

1. A method of screening a catechin or antibody to determine whether the catechin or antibody has the same pharmacological effect as that of epigallocatechin gallate, which comprises the steps of qualitatively or quantitatively determining the degree of binding of epigallocatechin gallate and the catechin or antibody to a full length 67 kDa laminin receptor expressed on the cell surface of cancer cells, determining that the degree of binding of the catechin or antibody to the full length 67 kDa laminin receptor expressed on the cell surface of cancer cells is higher than that of binding of the epigallocatechin gallate to the full length 67 kDa laminin receptor expressed on the cell surface of cancer cells, and determining that the catechin or antibody displaces the binding of epigallocatechin gallate to displacement of the binding of epigallocatechin gallate by the catechin or antibody indicates that the screened catechin or antibody has the same pharmacological effect as that of the epigallocatechin gallate, wherein the pharmacological effect of the epigallocatechin gallate is a growth-inhibiting effect on cancer cells.

3. The screening method as claimed in claim 1, wherein the method is a method of screening an antibody.

4. The screening method as claimed in claim 2, wherein the method is a method of screening an antibody.

5. The screening method as claimed in claim 1, wherein the method is a method of screening a catechin.

6. The screening method as claimed in claim 2, wherein the method is a method of screening a catechin.

* * * * *